(12) United States Patent
Blicke et al.

(10) Patent No.: US 8,133,195 B2
(45) Date of Patent: Mar. 13, 2012

(54) DEVICE FOR HANDLING BLOOD IN EXTRACORPOREAL BLOOD CIRCULATION

(75) Inventors: Rainer Blicke, Bitz (DE); Ulrich Haag, Bisingen (DE); Enno-Utz Kueper, Dusslingen (DE)

(73) Assignee: Maquet Cardiopulmonary AG, Hirrlingen (DE)

( * ) Notice: Subject to any disclaimer, the term of this patent is extended or adjusted under 35 U.S.C. 154(b) by 491 days.

(21) Appl. No.: 11/480,620

(22) Filed: Jul. 3, 2006

(65) Prior Publication Data

US 2007/0009378 A1  Jan. 11, 2007

(30) Foreign Application Priority Data

Jul. 6, 2005 (DE) .................. 10 2005 031 582

(51) Int. Cl.
- *A61M 37/00* (2006.01)
- *B01D 11/00* (2006.01)
- *B01D 61/00* (2006.01)

(52) U.S. Cl. .............. 604/6.09; 604/6.13; 604/6.14; 210/646; 210/647

(58) Field of Classification Search .............. 422/44–47, 422/48; 210/645, 646
See application file for complete search history.

(56) References Cited

U.S. PATENT DOCUMENTS

| | | | |
|---|---|---|---|
| 4,396,584 A | 8/1983 | Burgess et al. | |
| 4,424,190 A | 1/1984 | Mather, III et al. | |
| 5,043,140 A | 8/1991 | Combs et al. | |
| 5,270,005 A | 12/1993 | Raible | |
| 5,411,706 A | 5/1995 | Hubbard et al. | |
| 5,429,184 A | 7/1995 | Bach et al. | |
| 5,770,149 A | 6/1998 | Raible et al. | |
| 5,823,987 A | 10/1998 | Elgas et al. | |
| 6,241,945 B1 | 6/2001 | Owen | |
| 6,451,257 B1 * | 9/2002 | Flamer | 422/44 |
| 2002/0032405 A1 * | 3/2002 | Sweezer | 604/96.01 |
| 2003/0098146 A1 * | 5/2003 | Angermann et al. | 165/167 |
| 2004/0009097 A1 * | 1/2004 | Stringer et al. | 422/45 |
| 2005/0192525 A1 * | 9/2005 | Wieting et al. | 604/6.09 |

FOREIGN PATENT DOCUMENTS

| | | |
|---|---|---|
| DE | 37 33 542 | 7/1988 |
| DE | 39 23 692 | 1/1991 |
| DE | 42 38 884 | 5/1994 |
| EP | 0 987 035 | 3/2000 |
| EP | 1 382 358 | 1/2004 |
| EP | 1382358 A1 * | 1/2004 |
| EP | 1 464 350 | 10/2004 |
| EP | 1 465 350 | 10/2004 |
| EP | 1 550 473 | 7/2005 |
| JP | 052780/1974 | 5/1974 |
| JP | 104617/1988 | 5/1988 |
| JP | 8-312536 | 11/1996 |
| JP | 2004-154425 | 6/2004 |
| WO | 93/01846 | 2/1993 |
| WO | 01/83000 | 11/2001 |
| WO | 04/101021 | 12/2003 |

* cited by examiner

*Primary Examiner* — Melanie Hand
(74) *Attorney, Agent, or Firm* — Michael J. Striker

(57) ABSTRACT

In a device for handling blood in extracorporeal blood circulation that has at least one oxygenator, one heat exchanger, and one blood filter, the inlets and outlets in the oxygenator/heat exchanger unit are embodied such that a blood flow cross section of $A \geq 80$ mm$^2$, preferably $A \geq 120$ mm$^2$, is assured. The device can also be operated in an isolated form as a single structural part, which takes on the functions of an oxygenator and a heat exchanger with a blood filter. If a pump is provided in the device, then the pump drive can be removed as needed.

6 Claims, 2 Drawing Sheets

DEVICE FOR HANDLING BLOOD IN EXTRACORPOREAL BLOOD CIRCULATION

CROSS-REFERENCE TO A RELATED APPLIACTION

The invention described and claimed hereinbelow is also described in German Patent Application DE 10 2005 031 582.8 filed on Jul. 6, 2005. This German Patent Application, whose subject matter is incorporated here by reference, provides the basis for a claim of priority of invention under 35 U.S.C. 119(a)-(d).

BACKGROUND OF THE INVENTION

The invention relates to a device for handling blood in extracorporeal blood circulation that has at least one oxygenator, one heat exchanger, and one blood filter.

One such device has become known from European Patent Disclosure EP 1 465 350 A1.

The known device, in a housing, has a bubble trap, a blood pump, a heat exchanger, an oxygenator, and an arterial blood filter. The individual device components are coupled tightly together, so that shorter line courses are attained, compared to components that are fluidically connected to one another via line systems. The line courses themselves, however, are also constrictions which put a burden on the blood to be processed, so that these cross sectional constrictions are a hindrance to gentle blood processing.

SUMMARY OF THE INVENTION

The object of the invention is to refine a device for handling blood in extracorporeal blood circulation in such a way that on the one hand it can be used safely, reliably, and securely as well as quickly for broadened indications, and on the other, it handles the blood circulating outside the body as gently as possible.

According to the invention, this object is attained with A device for handling blood in extracorporeal blood circulation has at least one oxygenator; at least one heat exchanger which together with said at least one oxygenator forms an oxygenator/heat exchanger structural unit having an inlet and an outlet, wherein said inlet and outlet into said oxygenator/heat exchanger unit has a blood flow cross-section of $A \geqq 80 \text{ mm}^2$; and a blood filter coupleable to said structural unit and having a blood flow cross-section which corresponds to said blood flow cross-section of said structural unit.

The device components represented by the oxygenator, heat exchanger and blood filter, because connecting lines or conduits are dispensed with, form a compact module in one housing.

The device of the invention thus has the substantial advantage that constrictions inside the device when blood is being handled are minimized; the blood to be processed can flow between the device components over wide flow cross sections and as a result experiences considerably less shear stress than in flow courses known from the prior art, which involve connecting lines or directly communicating conduits between two device components. Because connecting lines or conduits that narrow the blood pathway are dispensed with, the pressure drop along the device is minimized, with an attendant reduction in the necessary pumping capacity and correspondingly reduced damage to the blood.

Moreover, because of the compact construction, the blood volume circulating outside the body is reduced, as is the fluid volume needed for priming, that is, for putting the compact module into operation. The dwell time of the blood circulating outside the body is shortened considerably as a result of the embodiment according to the invention of the inlets and outlets of the device components, since large inlet and outlet cross sections of the device components are coupled together directly, and hence pressure losses inside the device of the invention are minimized. If the blood flow cross sections are designed to be greater than and/or equal to $120 \text{ mm}^2$, and this is always true at the transition region of the device components to one another, then the blood circulating outside the body is still further protected, and shear forces acting on the blood and the pressure acting fluidically on the blood are minimized. Thus the device of the invention can be operated with a lower pump capacity, which acts to counter factors that would damage the blood.

In a further feature of the invention, the heat exchanger is integrated with the oxygenator, and the oxygenator and the heat exchanger form an inseparable structural part. This has the advantage that a very effective heat exchanging capacity can be attained, for instance by the integration of heat exchanger fibers in the oxygenator. The heat exchanger fibers can for instance divert electrostatic charges even more effectively, and they improve the capacity of the heat exchanger. In the embodiment according to the invention, the heat exchanger and the oxygenator form an inseparable structural part, and the function components of the heat exchanger and the oxygenator form a single unit. This makes a very compact construction possible and improves the efficiency of the cooperation of the heat exchanger and the oxygenator.

In a further feature of the invention, the inlet and/or outlet of the blood has a plurality of openings, which are distributed over the circumference of the structural unit or structural part. If the structural part experiences an oncoming flow via a plurality of openings, the blood flow is introduced uniformly into the device of the invention, and a patient's blood that is to be processed is handled especially gently.

In a further feature of the invention, the openings have opening cross sections of different sizes. This has the advantage that large openings in the upper part of the structural part can be better used for removing gas bubbles from the blood. As needed and depending on the structural design of the structural part, the openings can be placed at the most various points of the structural part and thus even structural part optimization that is not possible when there is only a single inlet and a single outlet is also supported.

Special advantages are obtained whenever four openings are provided over the circumference of the structural unit or structural part. By way of four openings, not only can line systems transport the blood to be processed into the oxygenator/heat exchanger unit especially gently and quickly, but also the openings permit a direct communication with adjacent device components.

A pump, in particular a centrifugal pump, can be provided at the inlet or inlets of the structural part or structural unit, by way of which pump the blood to be processed flows into the oxygenator/heat exchanger. The outlet or outlets of the pump are adapted to the inlet or inlets of the structural unit or structural part, so that without a pressure loss, the blood to be processed can flow from the pump into the oxygenator/heat exchanger unit.

Special advantages are obtained whenever openings are present both in the upper part of the device and in the lower part of the device. The openings in the upper part of the device make simple and effective bevel-free filling of the centrifugal pump possible, while the openings on the lower part of the device make simple, complete evacuation of the pump chamber possible at the end of the extracorporeal blood circulation, when the blood located outside the body is supposed to be fed back into the patient as completely as possible.

If the centrifugal pump is coupled to the structural unit or structural part (the oxygenator/heat exchanger) via at least one connection, and if the connecting openings that carry the blood are located at the top and bottom, then regardless of the sizes of their opening cross sections, a preferred, simple and effective degassing or evacuation of the compact module is possible.

To assure short flow courses, the pump can be coupled directly to the structural unit or structural part. Lengthened line courses are prevented by this provision, and the entire device can be constructed in compact form as a result of this provision. A pump can be coupled as needed to the structural part or structural unit, so that such a device can be adapted in the simplest possible way to expanded range of use or to greater demands made of it.

If needed, it is also possible for a bubble trap or a blood reservoir, which is provided upstream of the pump and communicates fluidically with the pump to be provided on the structural unit or the structural part.

The device of the invention can thus be used for the most various uses for maintaining an extracorporeal blood circulation, and the device can be modified without requiring extremely complicated structural changes. All the device components can be united in a single housing, and a drive mechanism that does not come into contact with the blood to be processed can for instance be coupled to the pump.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
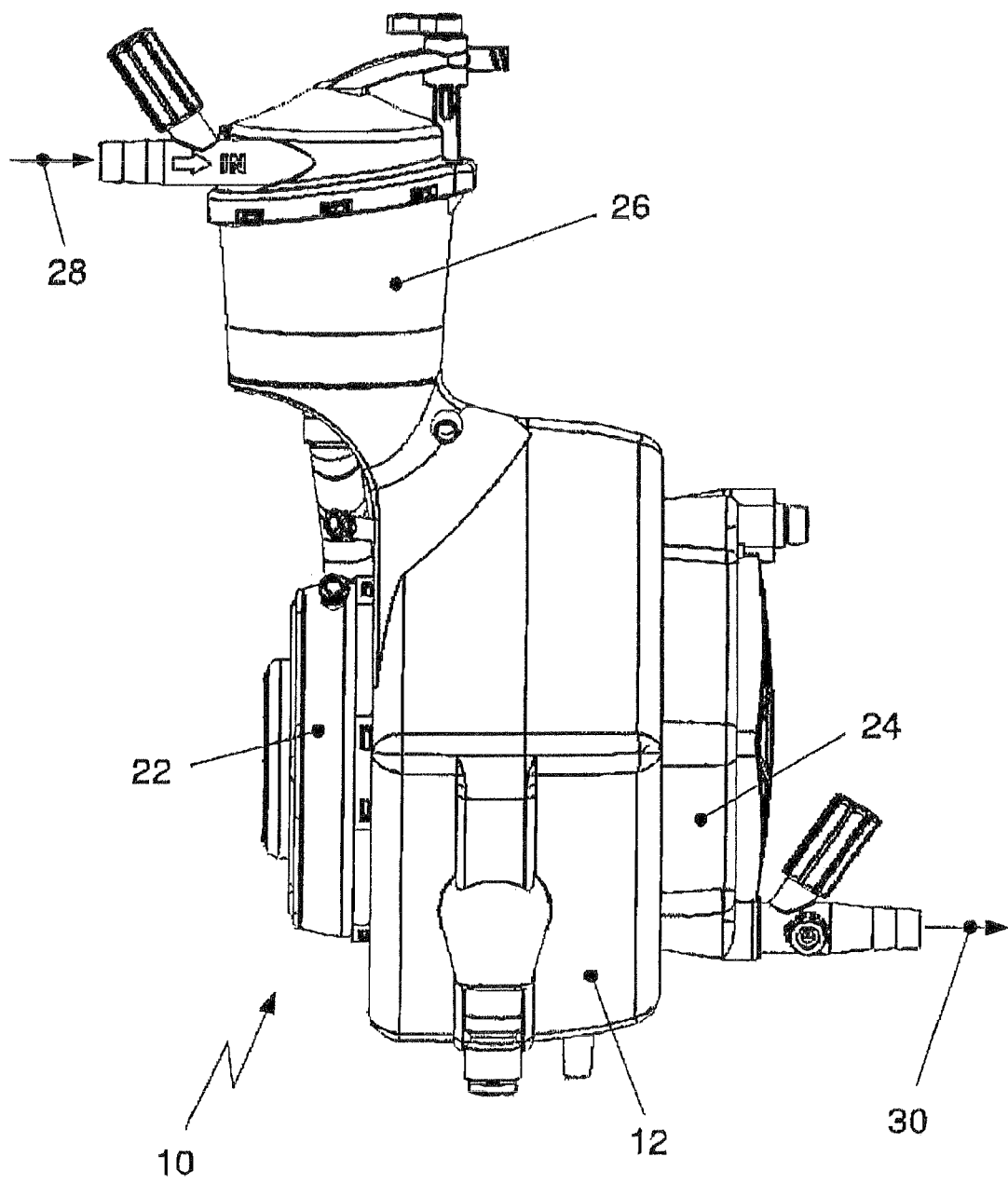
FIG. 1 is a side view showing one of several possible ways of embodying a device for holding blood in extracorporal blood circulation in accordance with the invention.
Figure 2:
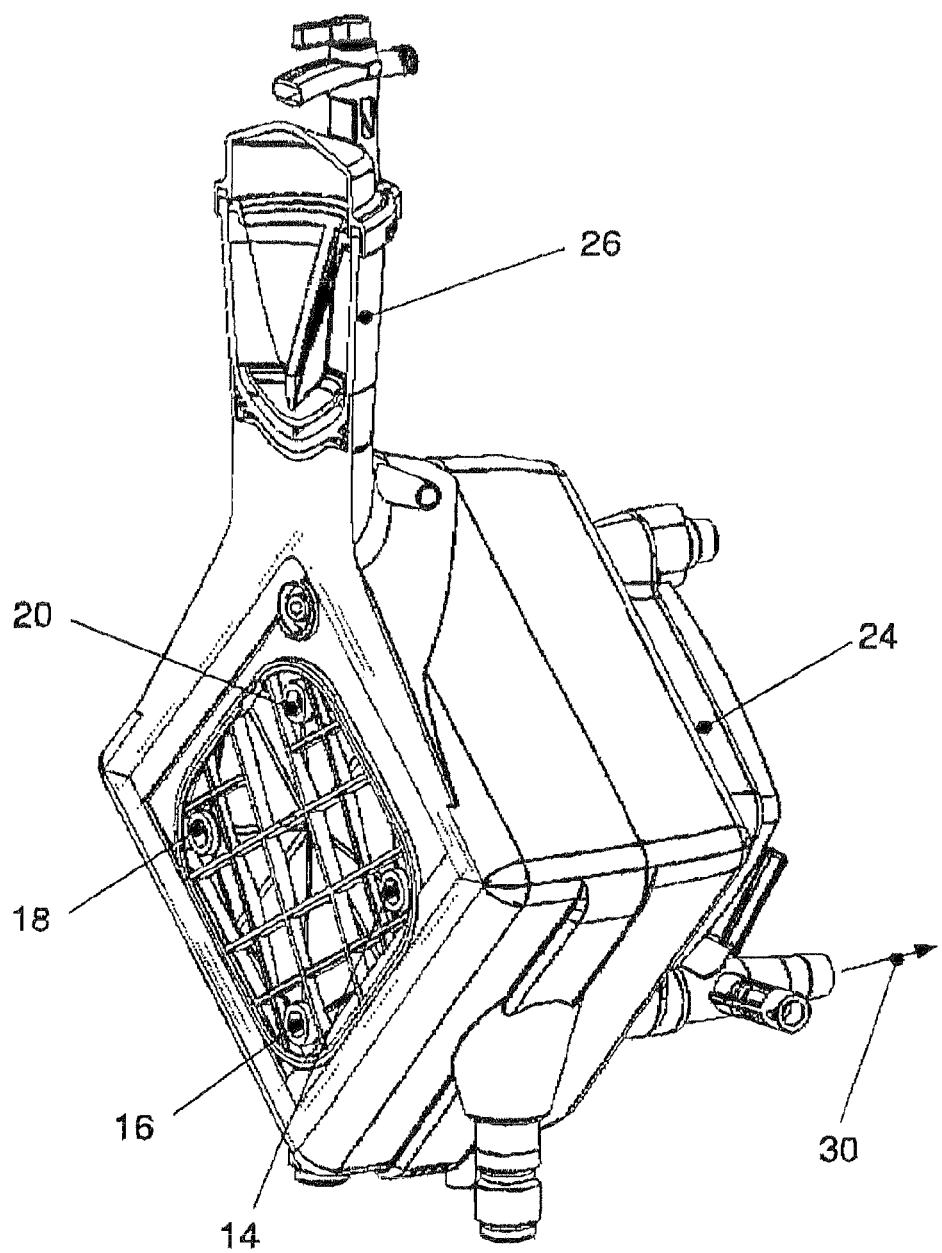
FIG. 2 is a perspective view of the device for holding blood in extracorporal blood circulation shown in FIG. 1.

In the drawing, an example of the device 10 of the invention is shown in a side view, with an oxygenator with which a heat exchanger is integrated, and the combination of equipment, which is meant to be considered a unit, is identified as structural part 12. At the inlet into the structural part 12, openings 14, 16, 18, 20 are provided, by way of which the blood to be processed, in this case venous blood, can flow into the structural part 12. The openings 14, 16, 18, 20 are embodied as needed in various sizes, so that for instance at the opening 20 preferentially, degassing of the blood flow is promoted. In the region of the openings 14, 16, 18, 20, locking means or connecting means are also provided between the device components.

In the drawing, a pump, in this case a centrifugal pump, is coupled directly to these openings 14, 16, 18, 20, so that without having to span lines, the blood to be processed can be pumped into the structural part 12 via the pump 22. The pump 22 has a drive mechanism that can be mounted on it and that makes it possible to operate the centrifugal pump in such a way that the drive mechanism does not come into contact with the blood to be processed (an example being a magnetic drive).

The openings 14, 16, 18, 20 shown in the drawing need not be distributed symmetrically over the inlet to the structural part 12. A single opening, which allows a blood flow cross section of $A \geqq 80$ mm$^2$ is for instance also conceivable. The blood flow cross sections created by the openings 14, 16, 18, 20 must in totality likewise allow a total blood flow cross section of $A \geqq 80$ mm$^2$.

At the outlet of the structural part 12, a plurality of openings are also embodied, which in the drawing are concealed because of the direct flanging onto the structural part 12; they too offer a blood flow cross section of $A \geqq 80$ mm$^2$. The inlet openings into a blood filter, flanged directly onto the structural part 12, are adapted to the outlet openings of the structural part 12, so that blood processed in the oxygenator/heat exchanger can flow into the blood filter 24 in as protected a way as possible and with the least possible stress.

A bubble trap 26 is provided on the housing of the structural part 12 and assures that only bubble-free blood will flow for processing into the centrifugal pump 22. The bubble trap 26 communicates fluidically with the pump 22, and the pump 22 communicates fluidically with the structural part 12. At least between the pump 22 and the structural part 12, there are no lines. The components shown in the drawing are flanged directly to the structural part 12, and the blood flow through the pump 22, the structural part 12 and the blood filter 24 is effected via conduits which are created directly as a result of the coupling of the various components of the device to the structural part 12.

Venous blood flows into the bubble trap 26 in the direction of the arrow 28, and arterial blood flows out of the device 10 of the invention in the direction of the arrow 30 and can be delivered directly to a patient.

The device 10 shown in the drawing can be operated if needed only via the structural part 12, namely an oxygenator with a heat exchanger integrated with it. The other device components, such as the pump 22, the blood filter 24 and the bubble trap 26, can optionally be used as needed. The entire device 10 can be integrated in a housing, so that according to the invention, a compact, safe device which does not allow mistaken operation is created.

In a device for handling blood in extracorporeal blood circulation that has at least one oxygenator, one heat exchanger 12, and one blood filter 24, the inlets and outlets in the oxygenator/heat exchanger unit are embodied such that a blood flow cross section of $A \geqq 80$ mm$^2$, preferably $A \geqq 120$ mm$^2$, is assured. The device 10 of the invention can also be operated in an isolated form as a single structural part 12, which takes on the functions of an oxygenator and a heat exchanger with a blood filter. If a pump 22 is provided in the device 10, then the pump drive can be removed as needed.

It will be understood that each of the elements described above, or two or more together, may also find a useful application in other types of constructions differing from the types described above.

While the invention has been illustrated and described as embodied in a device for handling blood in extracorporeal blood circulation, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A device for handling blood in extracorporeal blood circulation, comprising at least one oxygenator; at least one heat exchanger which together with said at least one oxygenator forms an oxygenator/heat exchanger structural unit having an inlet and an outlet, wherein said inlet and outlet into said oxygenator/heat exchanger unit has a blood flow cross-section of at least equal to 120 mm² minimizing shear stresses action on the blood; and a blood filter having an inlet provided on one side and coupled to said structural unit directly without connecting lines narrowing said blood flow cross-section and having a blood flow cross-section which is equal to said blood flow cross-section of said structural unit, wherein said blood flow cross-sections are at least equal to 120 mm², said filter also having an outlet provided on an opposite side for delivery of the blood, wherein said oxygenator, said heat exchanger, and said blood filter are connected with one another directly without connecting lines narrowing said blood flow cross-section, wherein said heat exchanger is composed of heat exchanger fibers and is integrated with said oxygenator, so that said oxygenator and said heat exchanger together form one structural part and the heat exchanger fibers are integrated in said oxygenator.

2. A device as defined in claim 1, further comprising a pump having an outlet directly connected with and adapted to said inlet of said structural unit.

3. A device as defined in claim 1, wherein said pump is a centrifugal pump.

4. A device as defined in claim 3; and further comprising at least one connection which couples said pump directly to said structural unit.

5. A device as defined in claim 1; and further comprising a bubble trap which is provided upstream of said pump, is connected with an inlet of said pump; and communicates fluidically with said pump.

6. A device as defined in claim 1; and further comprising a blood reservoir which is provided upstream of said pump and communicates fluidically with said pump.

* * * * *